United States Patent [19]

Hashimoto et al.

[11] 4,424,219

[45] Jan. 3, 1984

[54] 9-THIOMAYTANSINOIDS AND THEIR PHARMACEUTICAL COMPOSITIONS AND USE

[75] Inventors: Naoto Hashimoto; Hiroshi Shimadzu, both of Osaka, Japan

[73] Assignee: Takeda Chemical Industries, Ltd., Osaka, Japan

[21] Appl. No.: 374,158

[22] Filed: May 3, 1982

[30] Foreign Application Priority Data

May 20, 1981 [JP] Japan .................................. 56/76993

[51] Int. Cl.³ .................. A61K 31/535; C07D 498/06
[52] U.S. Cl. ......................... 424/248.54; 260/239.3 P
[58] Field of Search ..................... 260/239.37, 239.3 P; 424/248.54

[56] References Cited

U.S. PATENT DOCUMENTS

| 4,256,746 | 3/1981 | Miyashita et al. | 260/239.3 P |
| 4,260,608 | 4/1981 | Miyashita et al. | 260/239.3 P |
| 4,264,596 | 4/1981 | Miyashita et al. | 260/239.3 P |
| 4,307,016 | 12/1981 | Asai et al. | 260/239.3 P |
| 4,308,268 | 12/1981 | Miyashita et al. | 260/239.3 P |
| 4,308,269 | 12/1981 | Miyashita et al. | 260/239.3 P |
| 4,309,428 | 1/1982 | Miyashita et al. | 260/239.3 P |
| 4,317,821 | 3/1982 | Miyashita et al. | 260/239.3 P |

OTHER PUBLICATIONS

S. M. Kupchan et al., J. Med. Chem., 21, 31 (1978).
E. Higashide et al., Nature, 270, 721 (1977).

Primary Examiner—Robert T. Bond
Attorney, Agent, or Firm—Wegner & Bretschneider

[57] ABSTRACT

This invention relates to 9-thiomaytansinoid compounds represented by the formula

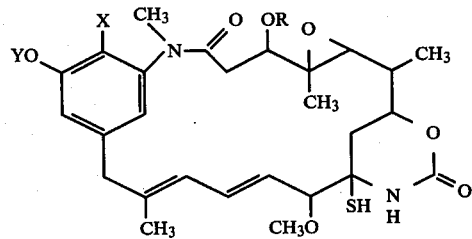

wherein R is hydrogen or acyl derived from a carboxylic acid, X is chlorine or hydrogen, Y is hydrogen, lower alkylsulfonyl, or alkyl or aralkyl which are unsubstituted or substituted, and methods of producing the same. The compounds are useful as antitumor, antiprotozoal and antifungal agents.

10 Claims, No Drawings

9-THIOMAYTANSINOIDS AND THEIR PHARMACEUTICAL COMPOSITIONS AND USE

This invention relates to novel maytansinoid compounds having antitumor activity.

Examples of maytansinoid compounds which have a macrocyclic lactam ring in common and show antitumor activity, include maytansine or colubrinol and related compounds which are obtainable from higher plants or antibiotic ansamitocins as the secondary matabolites of microorganisms. All of them have the same ansa macrolide skeleton and, as one of the principal active sites in the structure, the same cyclic carbinolamide moiety.

Kupchan, et al. [J. Med. Chem., 21, 31(1978)] have found that the hydroxyl group at 9-position of the cyclic carbinolamide moiety can be replaced with an alkoxy or alkylthio group in the presence of an acid catalyst. They synthesized 9-methoxy-, 9-ethoxy- and 9-propylthio derivatives of maytansine and maytanbutine. They have also found that these compounds, as compared with 9-hydroxyl-derivatives, showed significant decrease in their activity in antitumor experiments using P-388 leukemia, in inhibiting cell-division of KB-cells and Chinese hamster ovary cells (CHO), although they showed no significant decrease in the antimitotic activity against sea urchin eggs.

The present inventors succeeded in the production of novel 9-thiomaytansinoid compounds by converting the 9-hydroxy group of a maytansinoid compound to a 9-SH group with hydrogen sulfide or phosphorus pentasulfide, and confirmed that these novel compounds possess excellent antitumor activity, thus culminating in the present invention.

This invention is therefore concerned with maytansinoid compounds represented by the formula;

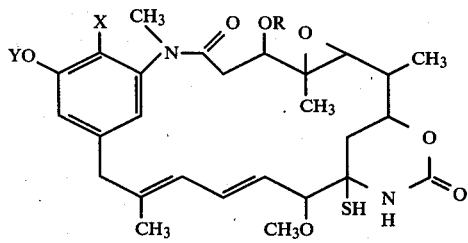
(I)

wherein R is hydrogen or acyl derived from a carboxylic acid, X is chlorine or hydrogen, Y is hydrogen, lower alkylsulfonyl, or alkyl or aralkyl which are unsubstituted or substituted.

Referring to the above formula (I), the acyl R derived from a carboxylic acid includes an acyl derived from a carboxylic acid having a molecular weight of up to about 300 or an acyl containing about 1 to 20 carbon atoms. The acyl thus includes, among others, saturated or unsaturated aliphatic acyl, saturated or unsaturated alicyclic acyl, aromatic acyl and N-acyl-α-amino acid acyl. These acyl may be represented by the following formula, for instance —COR[1]  (A)

wherein R[1] is hydrogen, alkyl, alkenyl, cycloalkyl or aryl, any of which may optionally be substituted, or the above-mentioned cyclic groups may be combined to the carbonyl through an alkylene chain.

Among these groups, those having substituents may for instance be N-acyl-α-aminoacyl of the following formula:

(B)

wherein $R^2$ is hydrogen, alkyl, cycloalkyl or aryl, any of which groups may optionally be substituted, or the cyclic groups may be combined to the α-carbon atom through an alkylene chain; $R^3$ is hydrogen, alkyl, cycloalkyl or aryl, any of which groups may optionally be substituted, or the cyclic groups may be combined to the N-atom through an alkylene chain; $R^4$ is hydrogen, alkyl, alkenyl, cycloalkyl, cycloalkenyl or aryl, any of which groups may optionally be substituted, or the cyclic groups may be combined to the carbonyl on the N-atom through the intermediary of an alkylene chain; $R^4$ may further be alkoxy or benzyloxy.

$R^1$ in the acyl designated by the above formula (A)  will now be described in detail.

The alkyl $R^1$ includes, among others, alkyl of about 1 to 18 carbon atoms (e.g. methyl, ethyl, propyl, isopropyl, butyl, isobutyl, sec-butyl, tert-butyl, pentyl, isopentyl, 1-methylpropyl, hexyl, heptyl, 3-heptyl, octyl, nonyl, decyl, undecyl, dodecyl, tridecyl, pentadecyl, heptadecyl) and, preferably, represents an alkyl of about 1 to 6 carbon atoms.

The alkenyl $R^1$ includes, among others, alkenyl of about 2 to 10 carbon atoms (e.g. vinyl, allyl, 1-methylvinyl, 2-methylvinyl, 1-octenyl, 1-decenyl) and, preferably, represents an alkenyl of about 2 to 4 carbon atoms.

The cycloalkyl $R^1$ includes, for example, cycloalkyls of about 3 to 10 carbon atoms (e.g. cyclopropyl, cyclobutyl, cyclopentyl, cyclohexyl, cycloheptyl, cyclooctyl, norbornyl, adamantyl).

The aryl group $R^1$ may for example be phenyl or naphthyl, and preferably is phenyl.

The alkyl, alkenyl, cycloalkyl and aryl, each represented by $R^1$, may optionally be substituted. The substituents may be such groups as, for example, alkoxy of 1 to 4 carbon atoms (e.g. methoxy, ethoxy, propoxy, isopropoxy, butoxy, isobutoxy, sec-butoxy, tert-butoxy), alkanoyl of 2 to 4 carbon atoms (e.g. acetyl, propionyl, butyryl, isobutyryl), alkanoyloxy of 2 to 4 carbon atoms (e.g. acetyloxy, propionyloxy, butyryloxy, isobutyloxy), alkoxycarbonyl of 2 to 4 carbon atoms (e.g. methoxycarbonyl, ethoxycarbonyl, propoxycarbonyl, isopropoxycarbonyl), halogens (e.g. chlorine, fluorine, bromine, iodine), hydroxyl, nitro, cyano, trifluoromethyl, amino, mono ($C_{1-4}$ alkyl)amino (e.g. methylamino), di($C_{1-4}$ alkyl)amino (e.g. dimethylamino, diethylamino, dipropylamino, diisopropylamino, dibutylamino), $C_{1-4}$ alkylthio (e.g. methylthio, ethylthio, propylthio, isopropylthio, butylthio, isobutylthio, sec-butylthio, tert-butylthio), $C_{1-4}$ alkylsulfinyl, $C_{1-4}$ alkanesulfonyl, oxo, thioxo, $C_{1-4}$ alkanoylamino (e.g. formamino, acetamino, propionylamino, butyrylamino, isobutyrylamino) and so forth. When $R^1$ is a cyclic group (cycloalkyl or aryl), there may be present such substituents as alkyls of 1 to 4 carbon atoms (e.g. methyl, ethyl, propyl, isopropyl, butyl, isobutyl, sec-butyl, tert-butyl). One to 3 of such substituents may be present, and may be the same or different.

The cyclic group $R^1$ (the cycloalkyl, or aryl which may optionally be substituted) may be combined to the carbonyl in the formula —$COR^1$ through an alkylene chain. The alkylene chain may for example be a straight-chain or branched alkylene of about 1 to 4 carbon atoms [e.g. methylene, ethylene, methylmethylene (ethylidene), propylene, butylene, 1-, 2- or 3-methylpropylene, 1- or 2-ethylethylene, propylmethylene, 1,1- or 1,2-dimethylethylene, isopropylmethylene]. Such alkylene chain may also have substituents similar to those mentioned above. Therefore, when said cyclic group is attached to the alkylene chain, $R^1$ represents a cycloalkylalkyl or aralkyl which may optionally be substituted.

Examples of the substituted $C_{1-18}$ alkyls as designated by $R^1$ include methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, butoxycarbonylethyl, fluoromethyl, chloromethyl, 2-chloroethyl, 3-chloropropyl, 4-chlorobutyl, trifluoromethyl, bromomethyl, 4-bromobutyl, 5-bromopentyl, iodomethyl, 2-iodoethyl, cyanomethyl, methylsulfinylethyl, methylsulfonylmethyl, etc.

The substituted alkenyl of 2 to 10 carbon atoms designated by $R^1$, may for example be 2-ethoxycarbovinyl.

The substituted $C_{3-10}$ cycloalkyl group $R^1$ includes, among others, 2,2-dimethylcyclopropyl, 4-isobutylcyclohexyl, 2-bromocyclopropyl, 2-chlorocyclobutyl, 4-chlorocyclohexyl, 2,2-difluorocyclobutyl, 3-methoxycyclohexyl, 4-acetylcyclohexyl, 2-cyanocyclobutyl, 4-cyanocyclohexyl, 4-dimethylaminocyclohexyl, etc.

The substituted aryl $R^1$ includes, among others, 2-, 3- or 4-methylphenyl, 4-tert-butylphenyl, 2-, 3- or 4-chlorophenyl, 2-, 3- or 4-bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl, 4-acetamidophenyl, etc.

When the cyclic group $R^1$ explained in detail as above [e.g. cycloalkyl or aryl (especially phenyl)] is combined to the carbonyl carbon of acyl group (A) through an alkylene chain, $R^1$ represents a combination of such a cyclic group and an alkylene, thus meaning, for example, cycloalkylalkyl or aralkyl. Such cycloalkylalkyl includes, for example, adamantylmethyl, cyclohexylmethyl, 3-cyclohexylpropyl, 2-cyclopentenylmethyl, 2-cyclopentenylethyl, etc. The aralkyl includes, for example, 4-bromobenzyl, 2-, 3- or 4-chlorobenzyl, 2,5- or 3,4-dimethoxybenzyl, 4-ethoxybenzyl, 4-fluorobenzyl, 3- or 4-methoxybenzyl, 4-methoxyphenylethyl, 1- or 2-naphtylmethyl, 2-, 3- or 4-nitrobenzyl, 3-nitrophenethyl, benzyl, 2-, 3- or 4-phenylpropyl, 2,3- or 4-methylbenzyl, 3,4,5-trimethoxybenzyl, α-methylphenethyl, etc.

The N-acyl-α-aminoacyl represented by the formula (B) will now be described.

The alkyl, alkenyl, cycloalkyl or aryl as represented by $R^2$, $R^3$, or $R^4$ may be the same as those mentioned for $R^1$. These groups may optionally be substituted and such substituents may be the same as those mentioned in connection with $R^1$. When the cyclic group $R^2$, $R^3$ or $R^4$ (i.e. cycloalkyl or aryl) may be attached, through an alkylene chain, to the α-carbon atom, N-atom or the carbonyl on the N-atom in the formula (B) and such alkylene chain may be the same as those mentioned hereinbefore in connection with $R^1$.

The alkoxy group $R^4$ may be an alkoxy of about 1 to 4 carbon atoms (e.g. methoxy, ethoxy, propoxy, isopropoxy, butoxy, isobutoxy, sec-butoxy, tert-butoxy.)

Referring, further, to the formula (B), the N-acyl-α-aminoacyl is typically exemplified by N-acetyl-N-methylglycyl, N-benzoyl-N-methylglycyl, N-(4-chlorobenzoyl)-N-methylglycyl, N-acetyl-N-methylalanyl, N-acetyl-N-benzylalanyl, N-acetyl-N-methylleucyl, N-isobutylyl-N-methylalanyl, N-isovaleryl-N-methylalanyl, N-propionyl-N-methylalanyl, N-acetyl-N-methylphenylalanyl, 2-(N-acetyl-N-methyl)-3-methoxycarbonylpropionyl, 2-(N-acetyl-N-methyl)amino-3-methylmercaptopropionyl, 2-(N-acetyl-N-methyl)amino-3-ethylmercaptopropionyl, N-acetyl-N-methylisoleucyl, N-acetyl-N-methylleucyl, N-acetyl-N-methylmethionyl, N-acetyl-N-methylphenylalanyl, N-acetyl-N-methyl-4'-acetoxytyrosinyl, N-benzyl-N-methylvalyl, N-acetyl-N-methylphenylglycyl, N-acetyl-N-methyl-3-cyanoalanyl, N-acetyl-N-methyl-(4'-dimethylamino)phenylalanyl, etc.

Referring to the above formula (I), the lower alkylsulfonyl designated by Y includes for example alkylsulfonyl containing about 1 to 4 carbon atoms (e.g. methanesulfonyl, ethanesulfonyl, 2-propanesulfonyl, 2-butanesulfonyl, butanesulfonyl).

Examples of the alkyl designated by Y include alkyl containing about 1 to 8 carbon atoms (e.g. methyl, ethyl, propyl, isopropyl, butyl, sec-butyl, pentyl, isopentyl, hexyl, heptyl, octyl), and examples of the aralkyl designated by Y include phenyl-$C_{1-3}$ alkyl (e.g. benzyl, 2-phenethyl, 3-phenylpropyl). The alkyl and aralkyl designated by Y may have substituents such as hydroxyl, amino, $C_{1-4}$ acylamino, $C_{1-4}$ alkyloxy, benzyloxy, oxo, halogen (e.g. chlorine, bromine, iodine), trifluoromethyl, methylenedioxy or $C_{1-4}$ alkylthio.

The compound (I) of this invention can be prepared by, for example, allowing a compound representable by the formula;

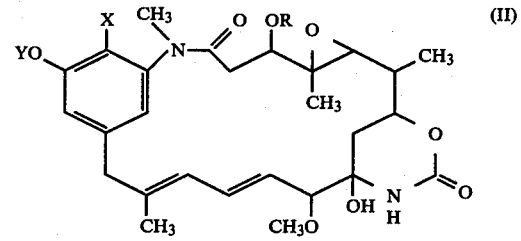

wherein each symbol is of the same meaning as defined above, to react with hydrogen sulfide or phosphorus pentasulfide.

The reaction of a compound of formula (II) with hydrogen sulfide is carried out in a solvent in the presence of an acid catalyst. Among such solvents are halogenated hydrocarbons (e.g. dichloromethane, chloroform), esters (e.g. ethyl acetate), ethers (e.g. dioxane, tetrahydrofuran, 1,2-dimethoxyethane), etc. The acid catalyst includes an organic strong acid, for example, trifluoroacetic acid, p-toluenesulfonic acid or methanesulfonic acid.

The reaction proceeds satisfactorily at a temperature ranging from 0° C. to 40° C. and preferably from about 5° C. to about room temperature. Hydrogen sulfide may be used in an amount of 5–100 times mol as much as the starting material, and the acid catalyst may be used in an amount of 2–10 times mol as much as the starting material.

The reaction of a compound (II) with phosphorus pentasulfide is carried out in the presence of tertiary amine. The amount of phosphorus pentasulfide is usually 1 to 30 times mol as much as the starting material, and preferably 1.5 to 5 times mol. The tertiary amine is exemplified by pyridine, picoline, lutidine, triethylamine, dimethylaniline or diethylaniline. The tertiary amine may be used in a volume sufficient for substantially dissolving the phosphorus pentasulfide used and serving not to make the reaction solution remarkably acid, but it may be used in a great excess even as the solvent. Besides, as solvents, the above-mentioned halogenated hydrocarbons, esters or ethers may be used. The reaction proceeds at temperatures ranging from about 0° C. to room temperature, but may be accelerated by heating at about 50° C. to 100° C.

The maytansinoid compound (I) thus produced can be isolated by subjecting the reaction mixture to a conventional procedure such as concentration, solvent extraction, chromatography, recrystallization, etc. When the desired compound is produced as a mixture of isomers (e.g. D- and L-isomers), the isomers can be separated from each other generally by a conventional procedure, e.g. silica gel column chromatography. The maytansinoid compound (I) according to this invention includes such individual isomers and all mixtures of the isomers.

The maytansinoid compound (I) according to this invention has strong anti-mitotic activity and antitumor activity, with comparatively low toxicity and therefore can be administered to warm blooded animals suffering from malignant tumors [e.g. leukemia (P-388, mouse), melanoma (B-16, mouse)] for prolongation of their survival time, thus can be used as an effective anti-tumor agent.

The compound (I) is normally administered safely, orally or parenterally, in the form of a suitable pharmaceutical preparation (e.g. injectable preparation) as formulated with a conventional carrier, diluent or the like. When compound (I) is administered as an injectable preparation, it may be applied by the subcutaneous, intraperitoneal, intravenous, intramuscular or other route as found suitable. The dosage may be decided from the range of about 0.01 to 2 mg/kg, preferably 0.025 to 1.6 mg/kg body weight, per dose, according to the condition and subject animal.

Such an injectable solution can be prepared by the established pharmaceutical procedure, e.g. by dissolving about 50 $\mu$g to 3 mg of (I) in about 0.5 ml of alcohol (e.g. ethanol) and making up the solution with physiological saline to obtain a total of 10 ml. When only a small dose is indicated, the above solution may be further diluted with physiological saline.

The compound (I) is useful also in that it displays antifungal and antiprotozoal activity. When (I) is used as an antifungal or/and antiprotozoal agent, it proves advantageous in testing a sample of soil, active sludge or animal body fluid for its bacterial flora. Thus, in such applications as the isolation of useful bacteria from soil samples and an assay of the activity of bacteria, to the exclusion of protozoa and fungi, in the operation and analysis of active sludge systems for waste water treatment, the compound (I) specifically allows the bacteria to grow without permitting growth of fungi and protozoa which may also be present in the specimens. A typical such procedure may comprise adding a test specimen to a liquid or solid medium, then adding to the medium 0.1 ml of about 10 to 100 $\mu$g/ml of compound (I) in water with 1% methanol per ml of the medium and incubating the mixture.

The compound (I), at the dose level of 0.02 ml as 1 mg/ml aqueous solution, inhibits growth of the causative microorganisms of stem rot, Helminthosporium leaf spot and sheath blight in rice plants and, therefore, can be used in the control of such plant diseases by spraying rice plants with a solution of compound (I) in 1% methanol-water, the concentration of which may range from about 0.5 to 5 $\mu$g/ml.

As the starting compound (II) employed in the method of this invention, the known plant-maytansinoid or ansamitocins can be used as they are, or maytansinol, dechloromaytansinol (U.S. Pat. No. 4,256,746) and 20-demethoxy-20-hydroxymaytansinol (U.S. Pat. No. 4,307,016) may be used as they are, or after acylation at 3-position or alkylation at 20-position by per se conventional manner.

The present invention will be explained more concretely by way of the following examples, reference examples, experimental examples and examples of pharmaceutical compositions, but they are not to limit its scope.

EXAMPLE 1

To 25 ml of dry pyridine in a vessel was added phosphorus pentasulfide (246 mg). The vessel was stoppered, and the mixture was stirred for a while at a room temperature. To the mixture was added 685 mg of ansamitocin P-3 dissolved in 25 ml of dry pyridine. The vessel was stoppered and the reaction mixture was stirred for about one hour at room temperature and then for four hours on an oil bath of 60°–70° C. The solvent was evaporated off under reduced pressure, and the residue was dissolved in ethyl acetate, washed four times with a sodium chloride solution then dried (Na$_2$SO$_4$). The solvent was evaporated off under reduced pressure, and the residue was subjected to a silicagel chromatography (solvent: ethyl acetate containing water) to separate a fraction containing 408 mg of the desired compound. This product was crystallized from ethyl acetate to yield 387 mg of 9-thioansamitocin P-3. Melting point: 192°–195° C. (decomp.).

NMR spectrum (CDCl$_3$)$\delta$: 0.81(3H,s), 1.19–1.31(9H,m), 1.68(3H,s), 2.76(1H,s), 3.13(3H,s), 3.34(3H,s), 3.97(3H,s), others.

Mass spectrum (m/e): 650(m+), 635, 616, 586, 572.

EXAMPLE 2

By a procedure analogous to that of Example 1, 20-demethoxy-20-hydroxyansamitosin P-3 (PDM-3) (267 mg) was allowed to react with 118.5 mg of phosphorus pentasulfide in 8 ml of dry pyridine. The reaction mixture was subjected to a work-up procedure analogous to that of Example 1. The resulting crude product was subjected to a silica-gel chromatography (solvent: ethyl acetate containing water) to separate a fraction containing 124 mg of the desired compound, which was crystallized from ethyl acetate to yield 49 mg of 9-thio-PDM-3. Melting point: 191°–193° C. (decomp.).

NMR spectrum (CDCl$_3$)$\delta$: 0.82(3H,s), 1.2–1.33(9H,m), 1.69(3H,s), 2.80(1H,s), 3.18(3H,s), 3.37(3H,s), others.

Mass spectrum (m/e): 602, 575, 558, 556.

EXAMPLE 3

By a procedure analogous to that of Example 1, maytansine (162 mg) was allowed to react with phosphorus pentasulfide (108 mg) in dry pyridine. The reaction mixture was subjected to a work-up procedure analogous to that of Example 1, then the resulting material was subjected to a silica-gel chromatography (solvent: ethyl acetate containing water) to separate a fraction containing the desired compound. The solvent was removed and the resulting product was crystallized from ethyl acetate to yield 59.8 mg of 9-thiomaytansine. Melting point: 190° C. (half melt), 192°–195° C. (decomp.).

NMR spectrum (CDCl$_3$)δ: 0.79(3H,s), 1.23–1.33(6H,m), 1.63(3H,s), 2.10(3H,s), 2.83(3H,s), 2.91(1H,s), 3.23(3H,s), 3.36(3H,s), 3.98(3H,s), others.

Mass spectrum (m/e): 707(M+), 692, 663, 629.

EXAMPLE 4

By a procedure analogous to that of Example 1, 205.6 mg of maytansinol was allowed to react with 168 mg of phosphorus pentasulfide in dry pyridine and the reaction mixture was worked-up as above, and chromatographed to yield 27.5 mg of 9-thiomaytansinol.

NMR spectrum (CDCl$_3$)δ: 0.83(3H,s), 1.17–1.33(9H,m), 1.68(3H,s), 2.81(1H,s), 3.22(3H,s), 3.37(3H,s), 3.99(3H,s), others.

Mass spectrum (m/e): 580(M+).

EXAMPLE 5

By a procedure analogous to that of Example 1, 62.4 mg of dechloroansamitocin P-3 was allowed to react with 50 mg of phosphorus pentasulfide in 5 ml of dry pyridine and the reaction mixture was worked-up and subjected to chromatographic separation to yield 15.8 mg of 9-thiodechloroansamitocin P-3.

NMR spectrum (CDCl$_3$)δ: 0.83(3H,s), 1.18–1.33(9H,m), 1.69(3H,s), 2.77(1H,s), 3.22(3H,s), 3.37(3H,s), 3.86(3H,s), 5.84(1H,t,J=1.5 Hz), others.

Mass spectrum (m/e): 616(M+)

EXAMPLE 6

To a solution of phosphorus pentasulfide (60 mg) in 7 ml of pyridine was added 85.5 mg of maytansinol 3-phenylacetate dissolved in 7 ml of pyridine. The reaction vessel was stoppered, and the mixture was stirred at room temperature for one hour, then heated at a temperature of 60°–70° C. for three hours on an oil bath. The reaction solution was worked-up by a procedure analogous to that in Example 1 and the resultant was purified by means of a silica-gel chromatography (solvent: ethyl acetate containing water) to yield 30.4 mg of 9-thiomaytansinol 3-phenylacetate, Melting point: 180°–183° C. (decomp.).

EXAMPLE 7

By a procedure analogous to Example 6, phosphorus pentasulfide (22 mg) was allowed to react with maytansinol 3-cyclobutanecarboxylate (25.1 mg) in 6 ml of pyridine and the reaction mixture was worked-up and then purified by means of a silica-gel chromatography to yield 10.6 mg of 9-thiomaytansinol 3-cyclobutanecarboxylate. Mass spectrum (m/e): 662(M+).

EXAMPLE 8

By a procedure analogous to Example 6, phosphorus pentasulfide (23.8 mg) was allowed to react with PDM-3 20-methanesulfonate (38.8 mg) in 6 ml of pyridine, and the reaction mixture was worked-up and, purified by means of a silica-gel chromatography to yield 26.6 mg of 9-thio PDM-3 20-methanesulfonate. Mass spectrum (m/e): 714(M+).

EXAMPLE 9

By a procedure analogous to Example 6, phosphorus pentasulfide (48 mg) was allowed to react with PDM-3 20-benzylether (69.7 mg) in 15 ml of pyridine and the reaction mixture was subjected to a work-up procedure as above. The resultant was purified by means of a silica-gel chromatography to yield 44.3 mg of 9-thio PDM-3 20-benzylether. Mass spectrum (m/e): 726(M+).

EXAMPLE 10

Ansamitocin P-3 (106 mg) was dissolved in 5 ml of dichloromethane. Hydrogen sulfide gas was bubbled through the solution for ten minutes with stirring under ice-cooling. To the resulting solution was added several drops of trifluoroacetic acid, and the mixture was stirred at room temperature overnight. The reaction mixture was washed with water and dried. The separation of the product was effected by means of a silica-gel chromatography (solvent: chloroform-methanol=from 100/1 to 50/1) to obtain 11 mg of 9-thioansamitocin P-3. Besides, 80 mg of ansamitocin P-3 (starting material) was recovered.

REFERENCE EXAMPLE

Method of preparing maytansinol 3-cyclobutanecarboxylate

Maytansinol (127.7 mg) and cyclobutanecarboxylic acid (120 μl) was dissolved in 5 ml of dichloromethane. To the solution, were added 340 mg of N,N-dicyclohexylcarbodiimide and 55 mg of 4-dimethylaminopyridine. The mixture was stirred at room temperature for four hours. To the reaction solution was added water, and the mixture was stirred. The resulting precipitates were removed by filtration and the filtrate was diluted with ethyl acetate. The ethyl acetate layer was separated and washed with water and dried. The solvent was removed by evaporation and the residue was purified by means of a silica-gel chromatography (solvent: aqueous ethyl acetate) to collect 82.7 g of a fraction containing the desired product. The product was crystallized from a small volume of ethyl acetate to yield 47.6 mg of maytansinol 3-cyclobutanecarboxylate. Melting point: 205°–208° C. (decomp.).

EXPERIMENTAL EXAMPLE

Antitumor activity

Therapeutic tests were carried out in mice according to NCI-protocols 1,200 and 1,300, Cancer Chemother, Reports, Part 3, 1972, Vol. 3, No. 2, in which leukemia P-388 and melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose ($\mu g/kg$) | Antitumor activities P-388 (T/C %) | B-16 (T/C %) |
|---|---|---|---|
| 9-Thioansamitocin P-3 (Example 1) | 800 | 106 | 65 |
| | 400 | 171 | 209 |
| | 200 | 171 | 190 |
| | 100 | 153 | 172 |
| 9-Thiomaytansine (Example 3) | 400 | 69 | 71 |
| | 200 | 153 | 195 |
| | 100 | 181 | 222 |
| | 50 | 178 | |

EXAMPLES OF PHARMACEUTICAL COMPOSITIONS

Example A

Composition for Injection

| | | |
|---|---|---|
| (1) 9-Thioansamitocin P-3 | 100 | mg |
| (2) Ethanol | 10 | g |
| (3) Polysorbate 80 (Tween 80) | 40 | g |
| (4) Mannitol | 20 | g |
| (5) Distilled water, a sufficient quantity to make | 1000 | ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

Example B

Composition for Injection

| | | |
|---|---|---|
| (1) 9-Thiomaytansine | 100 | mg |
| (2) Ethanol | 5 | g |
| (3) Polysorbate 80 (Tween 80) | 100 | g |
| (4) Mannitol | 20 | g |
| (5) Distilled water, a sufficient quantity to make | 1000 | ml |

Preparation

By a similar procedure to that of Example A, an injectable solution of (1) is prepared.

What is claimed is:

1. A compound of the formula:

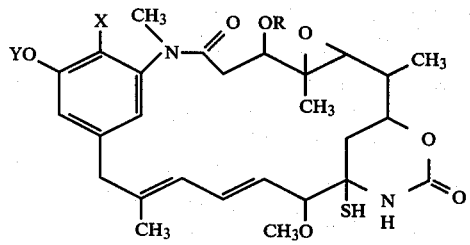

wherein R is hydrogen or $C_{1-20}$ acyl of the formula:

$-COR^1$ wherein $R^1$ is hydrogen, $C_{1-18}$ alkyl, $C_{2-20}$ alkenyl, $C_{3-10}$ cycloalkyl, phenyl or naphthyl, any of said groups being unsubstituted or substituted by $C_{1-4}$ alkoxy, $C_{2-4}$ alkanoyl, $C_{2-4}$ alkanoyloxy, $C_{2-4}$ alkoxycarbonyl, halogen, hydroxyl, nitro, cyano, trifluoromethyl, amino, mono($C_{1-4}$ alkyl)amino, di($C_{1-4}$ alkyl)amino, $C_{1-4}$ alkylthio, $C_{1-4}$ alkylsulfinyl, $C_{1-4}$ alkanesulfonyl, oxo, thioxo or $C_{1-4}$ alkanoylamino, said cycloalkyl, phenyl and naphthyl being attached, directly or through $C_{1-4}$ alkylene, to the carbonyl group in the acyl R, or R is of the formula:

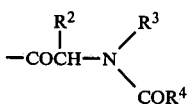

wherein $R^2$ is hydrogen, $C_{1-18}$ alkyl, $C_{1-10}$ cycloalkyl, phenyl, or naphthyl, $R^3$ is hydrogen, $C_{1-18}$ alkyl, $C_{3-10}$ cycloalkyl, phenyl or naphthyl, and $R^4$ is hydrogen, $C_{1-18}$ alkyl, $C_{2-10}$ alkenyl, $C_{3-10}$ cycloalkyl, phenyl or naphthyl, any of said groups in $R^2$, $R^3$ and $R^4$ being unsubstituted or substituted by $C_{1-4}$ alkoxy, $C_{2-4}$ alkanoyl, $C_{2-4}$ alkanoyloxy, $C_{2-4}$ alkoxycarbonyl, halogen, hydroxyl, nitro, cyano, trifluoromethyl, amino, mono($C_{1-4}$ alkyl)amino, di($C_{1-4}$ alkyl)amino, $C_{1-4}$ alkylthio, $C_{1-4}$ alkylsulfinyl, $C_{2-4}$ alkanesulfonyl, oxo, thioxo or $C_{1-4}$ alkanoylamino, and said cycloalkyl, cycloalkenyl, phenyl and naphthyl in $R^2$, $R^3$ and $R^4$ being attached, directly or through $C_{1-4}$ alkylene, to the $\alpha$-carbon atom, N-atom or the carbonyl group on the N-atom in R; X is chlorine or hydrogen; and Y is hydrogen, $C_{1-4}$ alkylsulfonyl, or $C_{1-8}$ alkyl or phenyl-$C_{1-4}$ alkyl which are unsubstituted or substituted by hydroxyl, amino, $C_{1-4}$ alkanoylamino, $C_{1-4}$ alkyloxy, benzyloxy, oxo, halogen, trifluoromethyl, $C_{2-5}$ alkoxycarbonyl, methylenedioxy or/and $C_{1-4}$ alkylthio.

2. The compound according to claim 1, wherein X is chlorine.

3. The compound according to claim 1, wherein $R^1$ is $C_{1-6}$ alkyl.

4. The compound according to claim 3, wherein $R^1$ is isopropyl.

5. The compound according to claim 1, wherein $R^2$, $R^3$ and $R^4$ are each $C_{1-6}$ alkyl.

6. The compound according to claim 5, wherein $R^2$, $R^3$ and $R^4$ are each methyl.

7. The compound according to claim 1, which is 9-thioansamitocin P-3.

8. The compound according to claim 1, which is 9-thiomaytansine.

9. A pharmaceutical composition for inhibiting the growth of tumor cells and prolonging the survival time of a warm-blooded animal, which contains an amount effective for that purpose of a compound of claim 2, 3, 4, 5, 6, 7, 8, or 1 and a pharmaceutically acceptable carrier, vehicle or diluent therefor.

10. A method for inhibiting the growth of tumor cells and prolonging the survival time of a warm-blooded animal, which comprises administering to said animal an effective amount of a compound of claim 2, 3, 4, 5, 6, 7, 8, or 1.

* * * * *